United States Patent
Wang

(10) Patent No.: US 11,318,268 B1
(45) Date of Patent: *May 3, 2022

(54) METHOD FOR CONTROLLING OXYGEN DELIVERED TO PATIENT IN OXYGEN THERAPY AND RELATED PRODUCTS

(71) Applicant: Telesair, Inc., Irvine, CA (US)

(72) Inventor: Qing Wang, Palo Alto, CA (US)

(73) Assignee: Telesair, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/465,116

(22) Filed: Sep. 2, 2021

Related U.S. Application Data

(63) Continuation of application No. 17/172,439, filed on Feb. 10, 2021, now Pat. No. 11,135,390.

(51) Int. Cl.
  *A61M 16/10* (2006.01)
  *A61M 16/00* (2006.01)
  *A61M 16/12* (2006.01)

(52) U.S. Cl.
  CPC ...... *A61M 16/101* (2014.02); *A61M 16/0066* (2013.01); *A61M 16/0069* (2014.02); *A61M 16/024* (2017.08); *A61M 16/12* (2013.01); *A61M 2016/1025* (2013.01); *A61M 2205/3331* (2013.01)

(58) Field of Classification Search
  CPC .............. A61M 16/00; A61M 16/0066; A61M 16/0069; A61M 16/024; A61M 16/10; A61M 16/1005; A61M 16/101; A61M 16/12; A61M 2016/1025; A61M 2205/3331; A61M 2205/3344
  See application file for complete search history.

(56) References Cited

U.S. PATENT DOCUMENTS

| | | | |
|---|---|---|---|
| 11,135,390 B1 * | 10/2021 | Wang | A61M 16/101 |
| 2002/0005197 A1 | 1/2002 | Devries et al. | |
| 2010/0116270 A1 | 5/2010 | Edwards et al. | |
| 2010/0224192 A1 * | 9/2010 | Dixon | A61B 5/02416 128/204.23 |
| 2012/0006326 A1 * | 1/2012 | Ahmad | A61M 16/024 128/204.22 |
| 2013/0087146 A1 | 4/2013 | Callaghan et al. | |
| 2016/0279378 A1 * | 9/2016 | Cipollone | A61M 16/207 |
| 2020/0179638 A1 * | 6/2020 | Oddo | A61M 16/0003 |
| 2021/0038855 A1 * | 2/2021 | Oddo | A61M 16/0051 |
| 2021/0308400 A1 * | 10/2021 | Sipes, Jr. | A61M 16/1055 |
| 2021/0316105 A1 * | 10/2021 | Godara | A61M 16/024 |

* cited by examiner

*Primary Examiner* — Joseph D. Boecker
(74) *Attorney, Agent, or Firm* — Maier & Maier, PLLC

(57) ABSTRACT

Provided are a method for controlling an oxygen provider and a portable device. The method includes: acquiring measurement data at a patient side; determining an oxygen demand volume and an output pattern of an oxygen provider based on the acquired measurement data and a desired oxygen fraction ratio; and controlling the oxygen provider with the oxygen demand volume and the output pattern. With the method or device for controlling an oxygen provider, oxygen with an amount that actually needed by a patient is provided to produce the blended gas to be delivered to the patient, and the blended gas delivered to the patient are regulated according to the output pattern to guarantee the blended gas is delivered in synchronization with the inspiration of the patient, so that a therapeutic effect is achieved with a lower oxygen consumption amount.

14 Claims, 5 Drawing Sheets

US 11,318,268 B1

METHOD FOR CONTROLLING OXYGEN DELIVERED TO PATIENT IN OXYGEN THERAPY AND RELATED PRODUCTS

CROSS-REFERENCE TO RELATED APPLICATIONS

This application is a continuation of U.S. patent application Ser. No. 17/172,439, filed on Feb. 10, 2021, which is hereby incorporated by reference in its entirety.

TECHNICAL FIELD

The present disclosure relates generally to the technical field of medical devices for oxygen therapy and, in particular, to a method for dynamically controlling oxygen provider and a portable device.

BACKGROUND

A respiratory disease often reduces a patient's oxygen level in blood, resulting in hypoxemia, a condition that damages heart, brain, and other human organs. When a patient's oxygen level in the blood is less than 95%, the patient needs to be treated with an oxygen therapy which requires an oxygen source, or production combined with storage.

High concentration oxygen (95% or above) provided by an oxygen source is often mixed with air to achieve target therapeutic fraction ratio of inspired oxygen ($FiO_2$), and delivered to a patient.

This background information is provided to reveal information believed by the applicant to be of possible relevance to the present disclosure. No admission is necessarily intended, nor should be construed, that any of the preceding information constitutes prior art against the present disclosure.

SUMMARY

The present disclosure provides a method for controlling an oxygen provider and related products.

A first aspect of the present disclosure relates to a method for controlling an oxygen provider is provided, including:
acquiring measurement data at a patient side;
determining an oxygen demand volume and an output pattern of an oxygen provider based on the acquired measurement data and a desired oxygen fraction ratio; and
controlling the oxygen provider with the oxygen demand volume and the output pattern.

In a possible implementation form of the method according to the first aspect as such, where the determining the oxygen demand volume and the output pattern of the oxygen provider based on the acquired measurement data and the desired oxygen fraction ratio includes:
determining a blended gas demand volume, an inspiration time and a breathing period based on the measurement data of the patient;
determining the oxygen demand volume based on the blended gas demand volume and the desired oxygen fraction ratio; and
determining the output pattern based on the blended gas demand volume, the inspiration time and the breathing period.

In a possible implementation form of the method according to the first aspect as such, where the oxygen provider includes an oxygen source and a blower device, and the output pattern includes a blower flow and a blowing period of the blower device;
the determining the output pattern based on the blended gas demand volume, the inspiration time and the breathing period includes:
determining the blower flow based on the blended gas demand volume and the inspiration time, and determining the blowing period based on the inspiration time and the breathing period;
the controlling the oxygen provider with the oxygen demand volume and the output pattern includes:
determining a duty cycle of the oxygen source based on the oxygen demand volume and the inspiration time;
controlling the oxygen source to operate according to the duty cycle; and
controlling the blower device to operate according to the blower flow and the blowing period.

In a possible implementation form of the method according to the first aspect as such, where the determining the oxygen demand volume based on the blended gas demand volume and the desired oxygen fraction ratio includes:
obtaining oxygen concentration measurement data at an output of the blower device;
and determining the oxygen demand volume based on the blended gas demand volume, the desired oxygen fraction ratio and the obtained oxygen measurement data.

In a possible implementation form of the method according to the first aspect as such, where the determining the blower flow based on the blended gas demand volume and the inspiration time includes:
obtaining flow measurement data at an output of the blower device; and
determining the blower flow based on the blended gas demand volume, the inspiration time and the obtained flow measurement data.

In a possible implementation form of the method according to the first aspect as such, where the measurement data includes flow measurement data and pressure measurement data;
the determining the blended gas demand volume, the inspiration time and the breathing period based on the measurement data of the patient includes:
determining whether a current phase is exhalation or inspiration;
in response to determining that the current phase is inspiration, determining the blended gas demand volume and the inspiration time based on at least one of the flow measurement data or the pressure measurement data;
in response to determining that the current phase is exhalation, determining an exhalation time based on at least one of the flow measurement data or the pressure measurement data; and
determining the breathing period based on the inspiration time and the exhalation time.

In a possible implementation form of the method according to the first aspect as such, where the in response to determining that the current phase is inspiration, determining the blended gas demand volume and the inspiration time based on at least one of the flow measurement data or the pressure measurement data includes:
in response to determining that the current phase is inspiration, triggering an inspiration timer and executing following steps until a first condition is satisfied:
calculating a patient flow and a maximum patient flow based on the flow measurement data; determining whether the patient flow is below a flow threshold, the flow threshold being determined based on the maximum patient flow; and in response to determining that the patient flow is blew the flow threshold, determining that the first condition is satisfied; otherwise, accumulating the patient flow as the blended gas demand volume and updating the flow measurement data;

when the first condition is satisfied, taking a value of the inspiration timer as the inspiration time and resetting the inspiration timer; and changing the current phase into exhalation.

In a possible implementation form of the method according to the first aspect as such, where the in response to determining that the current phase is inspiration, determining the blended gas demand volume and the inspiration time based on at least one of the flow measurement data or the pressure measurement data includes:

in response to determining that the current phase is inspiration, triggering an inspiration timer and executing following steps until a first condition is satisfied:

calculating a patient flow based on the flow measurement data;

calculating a current pressure and a baseline pressure based on the pressure measurement data; determining whether an increase of the current pressure from the baseline pressure is above a pressure rise threshold; and in response to determining that the increase of the current pressure is above the pressure rise threshold, determining that the first condition is satisfied; otherwise, accumulating the patient flow as the blended gas demand volume and updating the flow measurement data and the pressure measurement data;

when the first condition is satisfied, taking a value of the inspiration timer as the inspiration time and resetting the inspiration timer; and changing the current phase into exhalation.

In a possible implementation form of the method according to the first aspect as such, where the in response to determining that the current phase is exhalation, determining the exhalation time based on at least one of the flow measurement data or the pressure measurement data includes:

in response to determining that the current phase is exhalation, triggering an exhalation timer and executing following steps until a second condition is satisfied:

calculating a pressure change based on the pressure measurement data; determining whether the pressure change is above a pressure drop threshold; and in response to determining that the pressure change is above the pressure drop threshold, determining that the second condition is satisfied; otherwise, updating the pressure measurement data;

when the second condition is satisfied, taking a value of the exhalation timer as the exhalation time and resetting the exhalation timer; and changing the current phase into inspiration.

In a possible implementation form of the method according to the first aspect as such, where the in response to determining that the current phase is exhalation, determining the exhalation time based on at least one of the flow measurement data or the pressure measurement data includes:

in response to determining that the current phase is exhalation, triggering an exhalation timer and executing following steps until a second condition is satisfied:

calculating a patient flow increase based on the flow measurement data;

determining whether the patient flow increase is above a flow rise threshold; and in response to determining that the patient flow increase is above the flow rise threshold, determining that the second condition is satisfied; otherwise, updating the flow measurement data;

when the second condition is satisfied, taking a value of the exhalation timer as the exhalation time and resetting the exhalation timer; and changing the current phase into inspiration.

A second aspect of the present disclosure relates to a controlling device, the controlling device is communicatively connected to an oxygen provider, and the controlling device includes:

at least one processor; and a memory communicatively connected with the at least one processor; where, the memory stores instructions executable by the at least one processor, and the instructions, when executed by the at least one processor, cause the at least one processor to:

acquire measurement data at a patient side;

determine an oxygen demand volume and an output pattern of an oxygen provider based on the acquired measurement data and a desired oxygen fraction ratio; and control the oxygen provider with the oxygen demand volume and the output pattern.

In a possible implementation form of the controlling device according to the second aspect as such, where the at least one processor is caused to:

determine a blended gas demand volume, an inspiration time and a breathing period based on the measurement data of the patient;

determine the oxygen demand volume based on the blended gas demand volume and the desired oxygen fraction ratio; and determine the output pattern based on the blended gas demand volume, the inspiration time and the breathing period.

In a possible implementation form of the controlling device according to the second aspect as such, where the oxygen provider includes an oxygen source and a blower device, the oxygen source is communicatively connected to the controlling device and the blower device is connected to the oxygen source;

the output pattern includes a blower flow and a blowing period of the blower device;

the at least one processor is caused to determine the blower flow based on the blended gas demand volume and the inspiration time, and determine the blowing period based on the inspiration time and the breathing period;

the at least one processor is caused to:

determine a duty cycle of the oxygen source based on the oxygen demand volume and the inspiration time;

control the oxygen source to operate according to the duty cycle; and control the blower device to operate according to the blower flow and the blowing period.

In a possible implementation form of the controlling device according to the second aspect as such, where the at least one processor is caused to:

obtain oxygen concentration measurement data at an output of the blower device;

and determine the oxygen demand volume based on the blended gas demand volume, the desired oxygen fraction ratio and the obtained oxygen measurement data.

In a possible implementation form of the controlling device according to the second aspect as such, where the at least one processor is caused to:

obtain flow measurement data at an output of the blower device; and determine the blower flow based on the blended gas demand volume, the inspiration time and the obtained flow measurement data.

In a possible implementation form of the controlling device according to the second aspect as such, where the measurement data includes flow measurement data and pressure measurement data;

where the at least one processor is caused to:

determine whether a current phase is exhalation or inspiration;

in response to determining that the current phase is inspiration, determine the blended gas demand volume and the inspiration time based on at least one of the flow measurement data or the pressure measurement data;

in response to determining that the current phase is exhalation, determine an exhalation time based on the pressure measurement data; and determine the breathing period based on the inspiration time and the exhalation time.

In a possible implementation form of the controlling device according to the second aspect as such, where the at least one processor is caused to:

in response to determining that the current phase is inspiration, trigger an inspiration timer and execute following steps until a first condition is satisfied:

calculate a patient flow and a maximum patient flow based on the flow measurement data; determine whether the patient flow is below a flow threshold, the flow threshold being determined based on the maximum patient flow; and in response to determining that the patient flow is blew the flow threshold, determine that the first condition is satisfied; otherwise, the at least one processor is caused to:

accumulate the patient flow as the blended gas demand volume and update the flow measurement data;

when the first condition is satisfied, take a value of the inspiration timer as the inspiration time and reset the inspiration timer; and change the current phase into exhalation.

In a possible implementation form of the controlling device according to the second aspect as such, where the at least one processor is caused to:

in response to determining that the current phase is inspiration, trigger an inspiration timer and execute following steps until a first condition is satisfied:

calculate a patient flow based on the flow measurement data;

calculate a current pressure and a baseline pressure based on the pressure measurement data; determine whether an increase of the current pressure from the baseline pressure is above a pressure rise threshold; and in response to determining that the increase of the current pressure is above the pressure rise threshold, determine that the first condition is satisfied; otherwise, the at least one processor is caused to:

accumulate the patient flow as the blended gas demand volume and update the flow measurement data and the pressure measurement data;

when the first condition is satisfied, take a value of the inspiration timer as the inspiration time and reset the inspiration timer; and change the current phase into exhalation.

In a possible implementation form of the controlling device according to the second aspect as such, where the at least one processor is caused to:

in response to determining that the current phase is exhalation, trigger an exhalation timer and execute following steps until a second condition is satisfied:

calculate a pressure change based on the pressure measurement data; determine whether the pressure change is above a pressure drop threshold; and in response to determining that the pressure change is above the pressure drop threshold, determine that the second condition is satisfied; otherwise, the at least one processor is caused to:

update the pressure measurement data;

when the second condition is satisfied, take a value of the exhalation timer as the exhalation time and reset the exhalation timer; and change the current phase into inspiration.

In a possible implementation form of the controlling device according to the second aspect as such, where the at least one processor is caused to:

in response to determining that the current phase is exhalation, trigger an exhalation timer and execute following steps until a second condition is satisfied:

calculate a patient flow increase based on the flow measurement data; determine whether the patient flow increase is above a flow rise threshold; and in response to determining that the patient flow increase is above the flow rise threshold, determine that the second condition is satisfied; otherwise, the at least one processor is caused to:

update the flow measurement data;

when the second condition is satisfied, take a value of the exhalation timer as the exhalation time and reset the exhalation timer; and change the current phase into inspiration.

A third aspect of the present disclosure relates to a controlling device, the controlling device is communicatively connected to an oxygen provider, and the controlling device includes:

a detecting module, configured to acquire measurement data at a patient side;

a processing module, configured to determine an oxygen demand volume and an output pattern of an oxygen provider based on the acquired measurement data and a desired oxygen fraction ratio; and a controlling module, configured to control the oxygen provider with the oxygen demand volume and the output pattern.

In a possible implementation form of the controlling device according to the third aspect as such, where the processing module is configured to:

determine a blended gas demand volume, an inspiration time and a breathing period based on the measurement data of the patient;

determine the oxygen demand volume based on the blended gas demand volume and the desired oxygen fraction ratio; and determine the output pattern based on the blended gas demand volume, the inspiration time and the breathing period.

In a possible implementation form of the controlling device according to the third aspect as such, where the oxygen provider includes an oxygen source and a blower device, the oxygen source is communicatively connected to the controlling device and the blower device is connected to the oxygen source;

the output pattern includes a blower flow and a blowing period of the blower device;

the processing module is configured to determine the blower flow based on the blended gas demand volume and the inspiration time, and determine the blowing period based on the inspiration time and the breathing period;

the controlling module is configured to determine a duty cycle of the oxygen source based on the oxygen demand volume and the inspiration time; control the oxygen source to operate according to the duty cycle; and control the blower device to operate according to the blower flow and the blowing period.

In a possible implementation form of the controlling device according to the third aspect as such, where the processing module is configured to:

obtain oxygen concentration measurement data at an output of the blower device;

and determine the oxygen demand volume based on the blended gas demand volume, the desired oxygen fraction ratio and the obtained oxygen measurement data.

In a possible implementation form of the controlling device according to the third aspect as such, where the controlling module is configured to:

obtain flow measurement data at an output of the blower device; and determine the blower flow based on the blended gas demand volume, the inspiration time and the obtained flow measurement data.

In a possible implementation form of the controlling device according to the third aspect as such, where the measurement data includes flow measurement data and pressure measurement data;

where the processing module is configured to:

determine whether a current phase is exhalation or inspiration;

in response to determining that the current phase is inspiration, determine the blended gas demand volume and the inspiration time based on at least one of the flow measurement data or the pressure measurement data;

in response to determining that the current phase is exhalation, determine an exhalation time based on the pressure measurement data; and determine the breathing period based on the inspiration time and the exhalation time.

In a possible implementation form of the controlling device according to the third aspect as such, where the processing module is configured to:

in response to determining that the current phase is inspiration, trigger an inspiration timer and execute following steps until a first condition is satisfied:

calculate a patient flow and a maximum patient flow based on the flow measurement data; determine whether the patient flow is below a flow threshold, the flow threshold being determined based on the maximum patient flow; and in response to determining that the patient flow is blew the flow threshold, determine that the first condition is satisfied; otherwise, the processing module is configured to:

accumulate the patient flow as the blended gas demand volume and update the flow measurement data;

when the first condition is satisfied, take a value of the inspiration timer as the inspiration time and reset the inspiration timer; and change the current phase into exhalation.

In a possible implementation form of the controlling device according to the third aspect as such, where the processing module is configured to:

in response to determining that the current phase is inspiration, trigger an inspiration timer and execute following steps until a first condition is satisfied:

calculate a patient flow and a maximum patient flow based on the flow measurement data; determine whether the patient flow is below a flow threshold, the flow threshold being determined based on the maximum patient flow; and in response to determining that the patient flow is blew the flow threshold, determine that the first condition is satisfied; otherwise, the processing module is configured to:

accumulate the patient flow as the blended gas demand volume and update the flow measurement data;

when the first condition is satisfied, take a value of the inspiration timer as the inspiration time and reset the inspiration timer; and change the current phase into exhalation.

In a possible implementation form of the controlling device according to the third aspect as such, where the processing module is configured to:

in response to determining that the current phase is exhalation, trigger an exhalation timer and execute following steps until a second condition is satisfied:

calculate a pressure change based on the pressure measurement data; determine whether the pressure change is above a pressure drop threshold; and in response to determining that the pressure change is above the pressure drop threshold, determining that the second condition is satisfied; otherwise, the processing module is configured to:

update the pressure measurement data;

when the second condition is satisfied, take a value of the exhalation timer as the exhalation time and reset the exhalation timer; and change the current phase into inspiration.

In a possible implementation form of the controlling device according to the third aspect as such, where the processing module is configured to:

in response to determining that the current phase is exhalation, trigger an exhalation timer and execute following steps until a second condition is satisfied:

calculate a patient flow increase based on the flow measurement data; determine whether the patient flow increase is above a flow rise threshold; and in response to determining that the patient flow increase is above the flow rise threshold, determine that the second condition is satisfied; otherwise, the processing module is configured to:

update the flow measurement data;

when the second condition is satisfied, take a value of the exhalation timer as the exhalation time and reset the exhalation timer; and change the current phase into inspiration.

A fourth aspect of the present disclosure relates to a portable device, including a controlling device and an oxygen provider being communicatively connected to each other;

the controlling device includes at least one processor, and a memory communicatively connected with the at least one processor, where the memory stores instructions executable by the at least one processor, and the instructions, when executed by the at least one processor, cause the at least one processor to:

acquire measurement data at a patient side;

determine an oxygen demand volume and an output pattern of an oxygen provider based on the acquired measurement data and a desired oxygen fraction ratio; and control the oxygen provider with the oxygen demand volume and the output pattern.

In a possible implementation form of the portable device according to the fourth aspect as such, where the at least one processor is caused to:

determine a blended gas demand volume, an inspiration time and a breathing period based on the measurement data of the patient;

determine the oxygen demand volume based on the blended gas demand volume and the desired oxygen fraction ratio; and determine the output pattern based on the blended gas demand volume and the inspiration time.

In a possible implementation form of the portable device according to the fourth aspect as such, where the oxygen provider includes an oxygen source and a blower device, the oxygen source is communicatively connected to the controlling device and the blower device is connected to the oxygen source;

the output pattern includes a blower flow and a blowing period of the blower device;

the at least one processor is caused to determine the blower flow based on the blended gas demand volume and the inspiration time, and determine the blowing period based on the inspiration time and the breathing period;

the at least one processor is caused to:

determine a duty cycle of the oxygen source based on the oxygen demand volume and the inspiration time;

control the oxygen source to operate according to the duty cycle; and control the blower device to operate according to the blower flow and the blowing period.

In a possible implementation form of the portable device according to the fourth aspect as such, where the at least one processor is caused to:

obtain oxygen concentration measurement data at an output of the blower device; and determine the oxygen demand volume based on the blended gas demand volume, the desired oxygen fraction ratio and the obtained oxygen measurement data.

In a possible implementation form of the portable device according to the fourth aspect as such, where the at least one processor is caused to:

obtain flow measurement data at an output of the blower device; and determine the blower flow based on the blended gas demand volume, the inspiration time and the obtained flow measurement data.

In a possible implementation form of the portable device according to the fourth aspect as such, where the measurement data includes flow measurement data and pressure measurement data;

where the at least one processor is caused to:

determine whether a current phase is exhalation or inspiration;

in response to determining that the current phase is inspiration, determine the blended gas demand volume and the inspiration time based on at least one of the flow measurement data or the pressure measurement data;

in response to determining that the current phase is exhalation, determine an exhalation time based on the pressure measurement data; and determine the breathing period based on the inspiration time and the exhalation time.

In a possible implementation form of the portable device according to the fourth aspect as such, where the at least one processor is caused to:

in response to determining that the current phase is inspiration, trigger an inspiration timer and execute following steps until a first condition is satisfied:

calculating a patient flow and a maximum patient flow based on the flow measurement data; determining whether the patient flow is below a flow threshold, the flow threshold being determined based on the maximum patient flow; and in response to determining that the patient flow is blew the flow threshold, determine that the first condition is satisfied; otherwise, the at least one processor is caused to:

accumulate the patient flow as the blended gas demand volume and update the flow measurement data;

when the first condition is satisfied, take a value of the inspiration timer as the inspiration time and reset the inspiration timer; and change the current phase into exhalation.

In a possible implementation form of the portable device according to the fourth aspect as such, where the at least one processor is caused to:

in response to determining that the current phase is inspiration, trigger an inspiration timer and executing following steps until a first condition is satisfied:

calculate a patient flow based on the flow measurement data;

calculate a current pressure and a baseline pressure based on the pressure measurement data; determine whether an increase of the current pressure from the baseline pressure is above a pressure rise threshold; and in response to determining that the increase of the current pressure is above the pressure rise threshold, determine that the first condition is satisfied; otherwise, the at least one processor is caused to:

accumulate the patient flow as the blended gas demand volume and update the flow measurement data and the pressure measurement data;

when the first condition is satisfied, take a value of the inspiration timer as the inspiration time and reset the inspiration timer; and change the current phase into exhalation.

In a possible implementation form of the portable device according to the fourth aspect as such, where the at least one processor is caused to:

in response to determining that the current phase is exhalation, trigger an exhalation timer and execute following steps until a second condition is satisfied:

calculating a pressure change based on the pressure measurement data; determining whether the pressure change is above a pressure drop threshold; and in response to determining that the pressure change is above the pressure drop threshold, determining that the second condition is satisfied; otherwise, the at least one processor is caused to:

update the pressure measurement data;

when the second condition is satisfied, take a value of the exhalation timer as the exhalation time and reset the exhalation timer; and change the current phase into inspiration.

In a possible implementation form of the portable device according to the fourth aspect as such, where the at least one processor is caused to:

in response to determining that the current phase is exhalation, trigger an exhalation timer and execute following steps until a second condition is satisfied:

calculate a patient flow increase based on the flow measurement data; determine whether the patient flow increase is above a flow rise threshold; and in response to determining that the patient flow increase is above the flow rise threshold, determine that the second condition is satisfied; otherwise, the at least one processor is caused to:

update the flow measurement data;

when the second condition is satisfied, take a value of the exhalation timer as the exhalation time and reset the exhalation timer; and change the current phase into inspiration.

A fifth aspect of the present disclosure relates to a computer readable storage medium, storing thereon computer executable instructions which, when being executed by a processor, implement the method for controlling an oxygen provider according to the first aspect and the possible implementation forms.

DETAILED DESCRIPTION OF THE EMBODIMENTS

Figure 1:
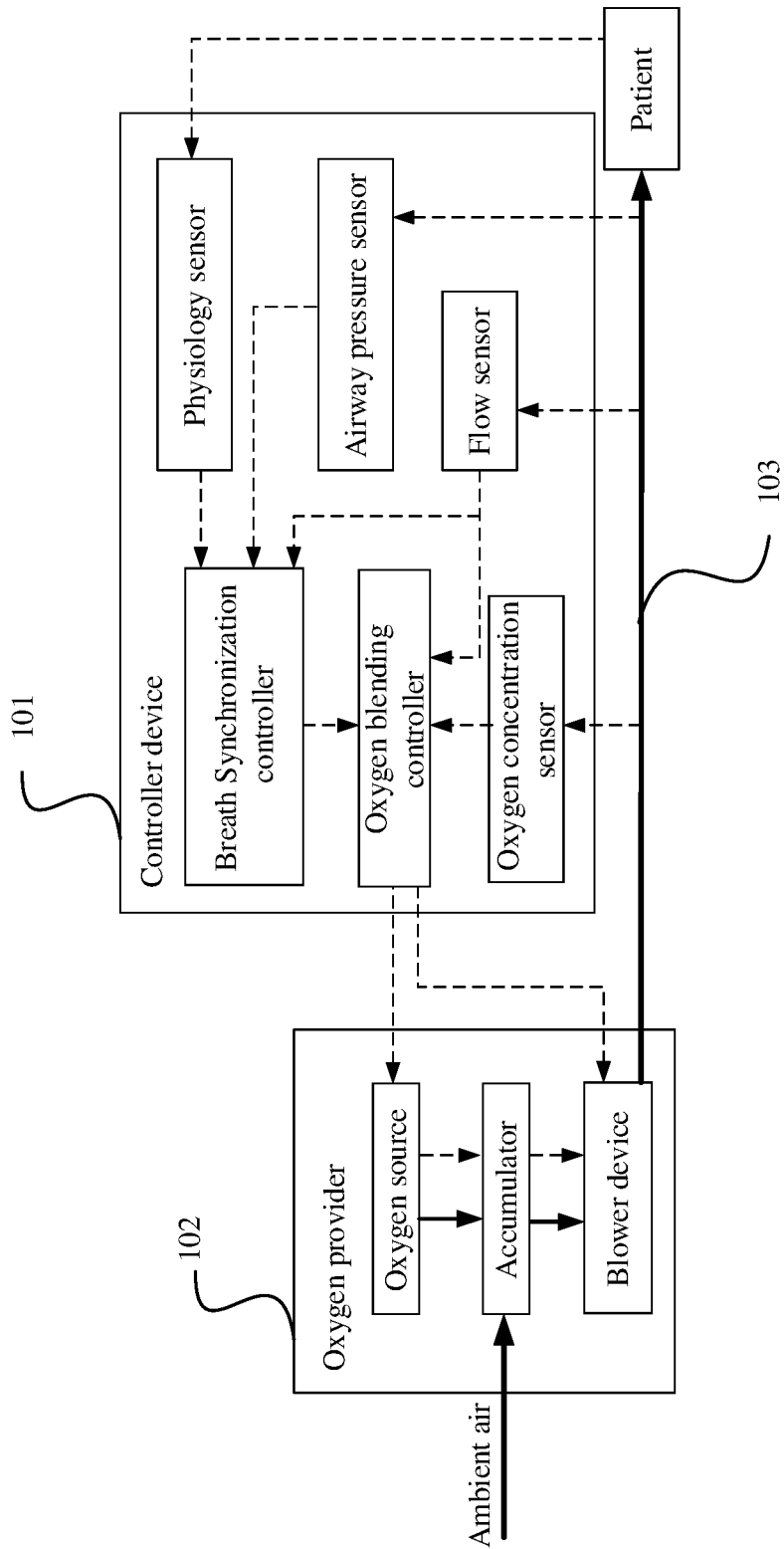
FIG. 1 is a schematic diagram of an oxygen delivering system according to an embodiment of the present disclosure.

In the following description, reference is made to the accompanying figures, which form part of the disclosure, and which show, by way of illustration, specific aspects of embodiments of the present disclosure or specific aspects in which embodiments of the present disclosure may be used. It is understood that embodiments of the present disclosure may be used in other aspects and comprise structural or logical changes not depicted in the figures. The following detailed description, therefore, is not to be taken in a limiting sense, and the scope of the present disclosure is defined by the appended claims.

For instance, it is understood that a disclosure in connection with a described method may also hold true for a corresponding device or system configured to perform the method and vice versa. For example, if one or a plurality of specific method steps are described, a corresponding device may include one or a plurality of units, e.g. functional units, to perform the described one or plurality of method steps (e.g. one unit performing the one or plurality of steps, or a plurality of units each performing one or more of the plurality of steps), even if such one or more units are not explicitly described or illustrated in the figures. On the other hand, for example, if a specific apparatus is described based on one or a plurality of units, e.g. functional units, a corresponding method may include one step to perform the functionality of the one or plurality of units (e.g. one step performing the functionality of the one or plurality of units, or a plurality of steps each performing the functionality of one or more of the plurality of units), even if such one or plurality of steps are not explicitly described or illustrated in the figures. Further, it is understood that the features of the various exemplary embodiments and/or aspects described herein may be combined with each other, unless specifically noted otherwise.

In the embodiments of the present disclosure, expressions such as "exemplary" or "for example" are used to indicate illustration of an example or an instance. In the embodiments of the present disclosure, any embodiment or design scheme described as "exemplary" or "for example" should not be interpreted as preferred or advantageous over other embodiments or design schemes. In particular, the use of "exemplary" or "for example" is aimed at presenting related concepts in a specific manner.

In an oxygen therapy, high concentration oxygen provided by an oxygen source is often mixed with air, so as to produce blended gas for delivering to a patient. Oxygen, as a key ingredient of the blended gas, needs to achieve a certain fraction ratio of inspired oxygen ($FiO_2$) to exert a therapeutic effect on the patient.

The volume of the blended gas supplied to a patient is often manually set and adjusted, for example, by a caregiver, however, the volume needed in an inspiration-expiration cycle for a patient may be contingent on various factors, such as disease severity, age, or a status of the patient (whether sleep or awake). If insufficient blended gas is delivered to the patient, the therapeutic effect may be compromised or even causing danger. And if excessive blended gas is delivered, a portion of oxygen will be wasted. Thus, it is desired that the volume delivered to a patient is determined or adjusted on a case by case basis.

A method for controlling an oxygen provider is described in the present disclosure. The aim of the method is to accurately determine the volume for high concentration oxygen as needed by a patient, and adjust the volume dynamically based on the determination, so as to achieve the therapeutic effect, as well as realizing more accurate control on the oxygen consumption amount to save costs.

Several terms that may be used herein are briefly explained before elaborating the present disclosure.

Oxygen, which refers to pure oxygen or high concentration oxygen that is used in an oxygen therapy.

Blended gas, which refers to a mixture of oxygen and air.

Gas, which is used as a general reference to oxygen, air or blended gas.

Flow, which refers to a gas volume per time unit in a specific location of airway from an oxygen source to a patient. For example, an inspiration flow refers to a flow that a patient breathes in from an airway.

An oxygen source, which refers to a piece of medical equipment that provides oxygen, including but not limited to a cylinder, a concentrator, an oxygen plant or a liquid oxygen supplier. Where, a cylinder is a refillable cylindrical storage vessel used to store and transport oxygen in compressed gas form; a concentrator is a self-contained, electrically powered medical device designed to concentrate oxygen from ambient air; an oxygen plant is an onsite oxygen generating system using pressure swing adsorption (PSA) which serves as a large, central source of oxygen generation, and can be located on-site at medical facilities; a liquid oxygen supplier contains bulk liquid oxygen generated offsite and stored in a large tank and supplied throughout a health facility pipeline system, and the tank requires refilling by liquid oxygen supplier.

An oxygen provider, which is a device or a system that provides blended gas. For example, an oxygen provider may include a low-pressure oxygen source which generates low-pressure oxygen, an accumulator where the low-pressure oxygen and ambient air are mixed to produce blended gas, and a blower device to blow the blended gas to a patient. The low-pressure oxygen source may be a concentrator, or a cylinder and a flow regulator, where the cylinder provides high-pressure oxygen and the flow regulator regulates compressed high-pressure oxygen to low-pressure oxygen, or a liquid oxygen supplier and a flow regulator which regulates liquid oxygen to low-pressure oxygen (in gas form). It should be noted that the accumulator may be a separate component which is connected between the oxygen source and the blower device, or it may also be formed on the blowing device, for example, it may be implemented as a hole on the blowing device, as long as oxygen provided by the oxygen source is mixed with air before being provided to the patient.

Inspiration/expiration and inhalation/exhalation, which refer to the action or the process of breathing in/out of a patient.

Breathing period, which refers a time span of a breathing in/out process for a patient. In embodiments of the present disclosure, a breathing in and out process is divided into two phases, which will be referred to as exhalation and inspiration, or an exhalation phase and an inspiration phase. Accordingly, a breathing period is a duration of the two phases, which is a sum of an inspiration time and an exhalation time.

In the following, the embodiments of the present disclosure will be elaborated in details with reference to the accompanying figures.

An embodiment of the present disclosure provides a method for controlling an oxygen provider. The executive subject matter of the method will be referred to as a controller or a controller device hereinafter.

FIG. 1 is an exemplary schematic diagram of an oxygen delivering system according to an embodiment of the present disclosure. The oxygen delivering system includes a controller device 101, an oxygen provider 102 and an airway 103 from the oxygen provider 102 to a patient.

In FIG. 1, the signal or data traffic among different entities is indicated by dash lines, and the gas flow is indicated by solid lines.

With reference to FIG. 1, the input signals of the controller device 101 may include signals generated from the patient, such as signals indicating various physiology parameters of the patient which may include but not limited to a blood pressure, a heart rate, a body temperature, an arterial hemoglobin oxygen saturation signal ($SpO_2$), an airway pressure, a flow of inspiration/expiration, a chest movement range of the patient etc.

The controller device outputs a controlling signal to the oxygen provider 102. The controlling signal may include that for switching on/off the oxygen source, and that for controlling the operation of the blower device.

In a possible implementation, the oxygen provider 102 includes an oxygen source, an accumulator and a blower device. The accumulator provides a chamber where oxygen output by the oxygen source is mixed with ambient air to produce blended gas, and the blended gas is delivered through the blower device and the airway 103 to the patient. The accumulator may be integrated with the oxygen source or the blower device, for example, as a chamber with a hole at an output of the oxygen source, or as a hole on the blower device. The accumulator may also be implemented as a separate component which may be connected to the oxygen source or the blower device, as long as oxygen provided by the oxygen source is mixed with air before being provided to the patient.

Additionally, in a possible implementation, the input signal of the controller device 101 may further include a signal generated from the blended gas as a feedback signal to form a closed-loop controlling solution, where the feedback signal may include that is indicating a pressure in the airway, an oxygen concentration or a flow of the blended gas, and will be explained in detail in embodiments hereinafter.

It is understood that, FIG. 1 is merely a logical schematic diagram of the oxygen delivering system, which shows an exemplary configuration of functional units and a signal circulation therein between. In a practical application scenario, the function units of the system may be implemented in various forms.

For example, the controller device 101 may be a compact device which is configured to implement the method provided in the present disclosure, for example, it may be a portable device which is connected between an oxygen provider 102 and a patient, serving as a component of an oxygen delivering system which includes a plurality of components that may be assembled or connected by a caregiver onsite.

Or, the controller device 101 may be integrated into an oxygen provider 102 as a hardware/software/firmware unit of the oxygen provider 102, where a circulation of the signal between the functional units may be as same as those shown in FIG. 1.

Figure 2:
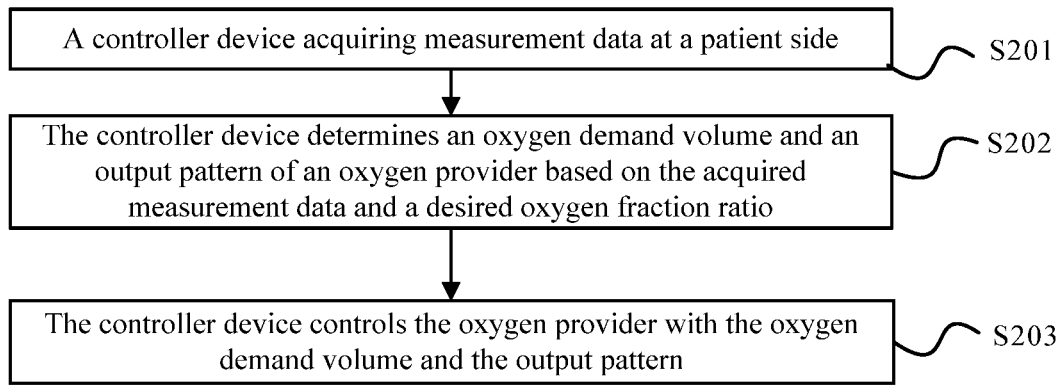
FIG. 2 is a schematic flowchart of a method for controlling an oxygen provider according to an embodiment of the present disclosure.

FIG. 2 is a schematic flowchart of a method for controlling an oxygen provider according to an embodiment of the present disclosure. The method may be applied in the oxygen delivering system shown in FIG. 1. The method includes the following steps:

Step 201, a controller device acquires measurement data at a patient side.

The measurement data may include various physiology parameters of the patient, which may indicate any physiology characteristic that is related to the volume of oxygen demanded by a patient (referred to as oxygen demand volume in the following description) in a breathing period or an inspiration phase. In a possible implementation, the measurement data includes data generated by physiology sensors attached to the patient, by devices with sensing functions, such as an airway pressure sensor, or by an airway flow sensor etc.

It is noted that, the physiology sensors may be integrated within the controller device, serving as a component of the controller device. Or, the physiology sensors and the controller device may be separated parts connected to each other.

Step 202, the controller device determines an oxygen demand volume and an output pattern of an oxygen provider based on the acquired measurement data and a desired oxygen fraction ratio.

The measurement data is used as input data of the controller device. A desired oxygen fraction ratio may be a default value or selected from a plurality of default values by a caregiver, or it may be a customized value input by a caregiver.

Figure 3:
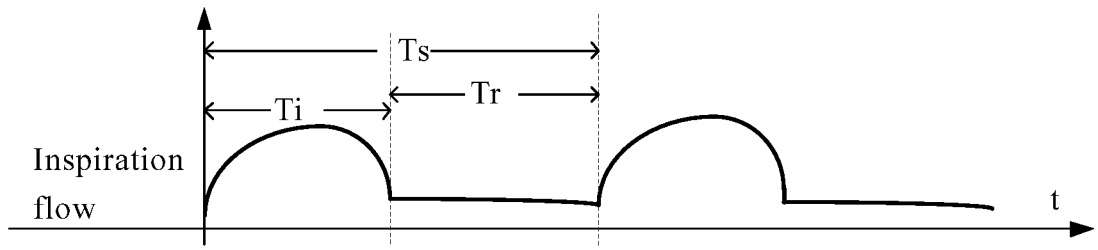
FIG. 3 is a schematic illustration of an inspiration flow of a patient as a function of time.

In a possible implementation, the oxygen demand volume is the oxygen volume that required for one breathing period (i.e., Ts as shown in FIG. 3), or for one time of inspiration (i.e. Ti as shown in FIG. 3). The oxygen demand volume may be determined by the controller device based on the measurement data and the desired oxygen fraction ratio.

For example, the controller device may acquire measurement data generated by the patient during at least one preceding breathing period and anticipate the oxygen demand volume for a following inspiration phase based on the acquired measurement data and the desired oxygen fraction ratio according to a predetermined algorithm. In the following inspiration phase, oxygen of that amount (defined by the oxygen demand volume) will be used to produce the blended gas to be delivered to the patient.

An example for the predetermined algorithm is explained in the following.

The controller device acquires measurement data generated by the patient during preceding P breathing period(s), where the measurement data includes flow measurement data of a patient interface (for example, a nasal airway) attached to the patient, and P is an integer greater than or equal to 1.

Additionally, the controller device determines a blended gas consumption volume of the patient for each of the P breathing period(s), and further determines that a blended gas demand volume for the following breathing period equals to an average value of the P blended gas consumption volume(s), or equals to the blended gas consumption volume of the previous one breathing period.

Furthermore, the controller device determines the oxygen demand volume based on the blended gas demand volume and the desired oxygen fraction ratio. For example, in a case where the oxygen source outputs pure oxygen, the oxygen demand volume may be calculated according to Equation 1.

$$L(O_2)=L(gas)*(FiO_2-21)/79 \qquad \text{Equation 1}$$

Where $L(O_2)$ is the oxygen demand volume, $L(gas)$ is the blended gas demand volume, $FiO_2$ is the desired oxygen fraction ratio. It is noted that, Equation 1 may have other variations adapting to different practical situations, for example, in a case where the oxygen source outputs 95% concentration oxygen, Equation 1 may be accordingly adapted as, for example, $L(O_2)[L(gas)*(FiO_2-21)/74$.

The output pattern of the oxygen provider is used for characterizing the working mode of the oxygen provider, and serves to regulate the blended gas delivered to the patient, so as to guarantee the blended gas being delivered to the patient during an inspiration phase. For example, the output pattern may be constrained at least by the timing and the flow for delivering the blended gas, that is, when the blended gas is to be delivered and how much of the blended gas is to be delivered (per time unit, or in a predetermined time span).

An inspiration flow of a patient as a function of time is shown in FIG. 3, a breathing period is denoted as Ts, an inspiration time is denoted as Ti, and an exhalation time is denoted as Tr, where Ts=Ti+Tr.

In a possible implementation, the controller device determines that the blended gas is delivered during the inspiration time Ti, that is, in every breathing period Ts, the blended gas is delivered during the Ti time span, and not delivered during the Tr time span.

In a possible implementation, the controller device calculates the flow for delivering the blended gas according to Equation 2.

$$F(gas)=L(gas)/Ti \qquad \text{Equation 2}$$

Where F(gas) is the flow for delivering the blended gas.

Step 203, the controller device controls the oxygen provider with the oxygen demand volume and the output pattern.

Figure 4:
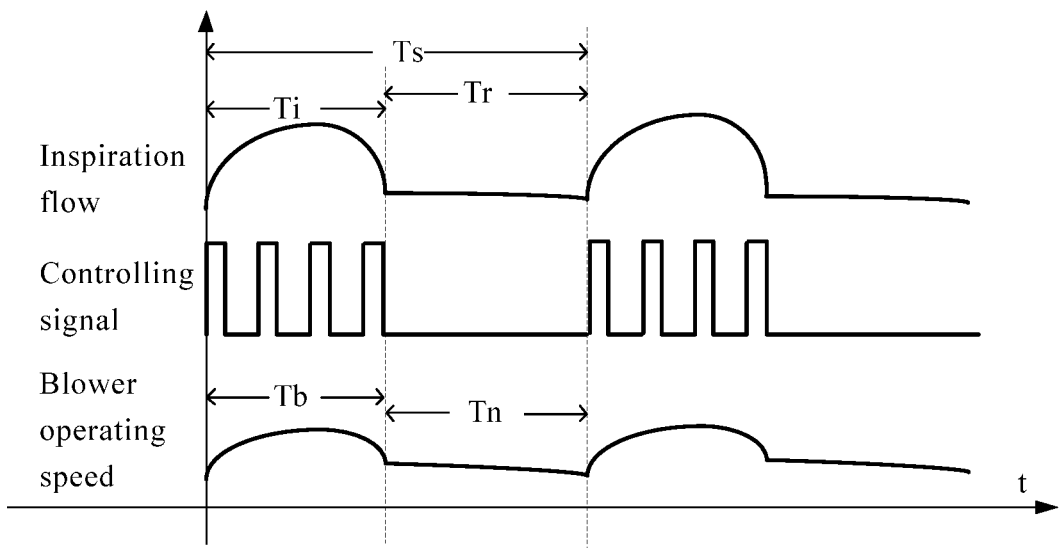
FIG. 4 is a schematic illustration of an inspiration flow, a controlling signal and blower operation according to an embodiment of the present disclosure.

In a possible implementation, the oxygen provider includes an oxygen source. With reference to FIG. 4, during the inspiration time Ti, the controller device may generate a controlling signal, for example, a square wave signal of a certain duty cycle to control the oxygen source to switch on and off repeatedly to produce the oxygen whose amount is defined by the oxygen demand volume. For example, when the square wave signal is of a relatively high amplitude, the oxygen source is switched on, and when the square wave signal is of a relatively low amplitude, the oxygen source is switched off. During the exhalation time Tr, the oxygen source may be switched off (the square wave signal is kept low). It is noted that the controlling signal may be an electrical signal or otherwise, as long as the controller device and the oxygen source are in communication connection and the oxygen source are controlled by the controller device.

The oxygen provider may further include an accumulator where the oxygen output by the oxygen source is mixed with ambient air to produce the blended gas whose amount is defined by the blended gas demand volume.

The oxygen provider may further include a blower device, and the output pattern may include a blower flow and a blowing period of the blower device.

The blower flow may be equal to F(gas) as calculated by Equation 2.

With reference to FIG. 4, the blowing period consists of a first time span Tb and second time span Tn. The blowing period may be equal to the breathing period Ts, and the first time span Tb may be equal to the inspiration time Ti. Accordingly, the second span Tn will be equal to the exhalation time Tr. In a possible implementation, the controller device controls the blower device to blow blended gas to the patient during the inspiration time Ti and to stop blowing during the rest of time of a breathing period Ts.

With reference to FIG. 1, the input signal of the controller device may further include signals generated from the blended gas as feedback signals to form a closed-loop controlling solution.

In a possible implementation, an oxygen concentration sensor is configured to detect an oxygen concentration of the blended gas in the airway (anywhere) between the blower device and the patient, for example, the oxygen concentration sensor may be attached at an output of the blower device. The controller obtains oxygen concentration measurement data generated by the oxygen concentration sensor, and calibrates the oxygen volume actually output by the oxygen source. The close-loop design is beneficial for ensuring the normal working of the controller, further, in case where the output of the blower device is abnormal, an alarming alert may be presented at the controller side so that the fault could be quickly detected.

For example, when the oxygen concentration feedback by the oxygen concentration sensor is lower than a first concentration threshold (which may be an empirical value or a value input by a caregiver, for example, $FiO_2*95\%$), the controller device increases the duty cycle of the square wave signal to increase the oxygen volume output by the oxygen source, which brings up the oxygen concentration at the output of the blower device.

When the oxygen concentration feedback by the oxygen concentration sensor is higher than a second concentration threshold (which may be an empirical value or a value input by a caregiver, for example, $FiO_2*105\%$), the controller device decreases the duty cycle of the square wave signal to decrease the oxygen volume output by the oxygen source, which brings down the oxygen concentration at the output of the blower device.

Based on the oxygen concentration feedback by the oxygen concentration sensor, the oxygen volume actually output by the oxygen source is calibrated to ensure that the oxygen delivering system operates effectively. Additionally, when the oxygen concentration feedback by the oxygen concentration sensor is out of the range from the first concentration threshold to the second concentration threshold for a time span which may be a predetermined value or a value input by a caregiver, the controller device may output a warning signal to alert the caregiver. The warning signal may be a sound alert, a text message or a call to a communication device which may be carried by a caregiver or installed at a nurse station etc.

In a possible implementation, a flow sensor is configured to detect the blended gas flow in the airway between the blower device and the patient, for example, the flow sensor may be attached at an output of the blower device. The controller obtains flow measurement data generated by the flow sensor, and calibrate the blended gas flow actually output by the blower device.

For example, when the blended gas flow feedback by the flow sensor is lower than a first delivery threshold (which may be an empirical value or a value input by a caregiver, for example, F(gas)*95%), the controller device controls the blower device to increase the blended gas flow at the output of the blower device.

When the blended gas flow is higher than a second delivery threshold (which may be an empirical value or a value input by a caregiver, for example, F(gas)*105%), the controller device controls the blower device to decrease the blended gas flow at the output of the blower device.

Based on the blended gas flow feedback by the flow sensor, the blended gas flow actually output by the blower device is calibrated to ensure that the oxygen delivering system operates effectively. Additionally, when the blended gas flow feedback by the flow sensor is out of the range from the first delivery threshold to the second delivery threshold for a time span which may be a predetermined value or a value input by a caregiver, the controller device may also output a warning signal.

It is noted that, the oxygen concentration sensor or the flow sensor may be integrated within the controller device to constitute a component of the controller device. Or, the oxygen concentration sensor or the flow sensor and the controller device may be separated parts connected to each other.

According to the method for controlling an oxygen provider explained in the embodiments of the present disclosure, an oxygen demand volume as needed by a patient and an output pattern of an oxygen provider are determined, and the oxygen provider is controlled with the oxygen demand volume and the output pattern.

In one breathing period, oxygen with an amount that actually needed by the patient is provided to produce the blended gas to be delivered to the patient, and the blended gas delivered to the patient is regulated according to the output pattern to guarantee the blended gas is delivered to the patient during the inspiration time span.

In one breathing period, the amount of oxygen provided to the patient, and the output pattern of the oxygen provider may be different from that of a previous breathing period based on variation of the measurement data acquired at the patient side, therefore, the amount of oxygen provided to the patient, and the output pattern of the oxygen provider may be dynamically adjusted.

In summary, the amount of oxygen actually needed by the patient is delivered and dynamically adjusted in synchronization with the inspiration of the patient, so that a therapeutic effect is achieved with a lower oxygen consumption amount.

Figure 5:
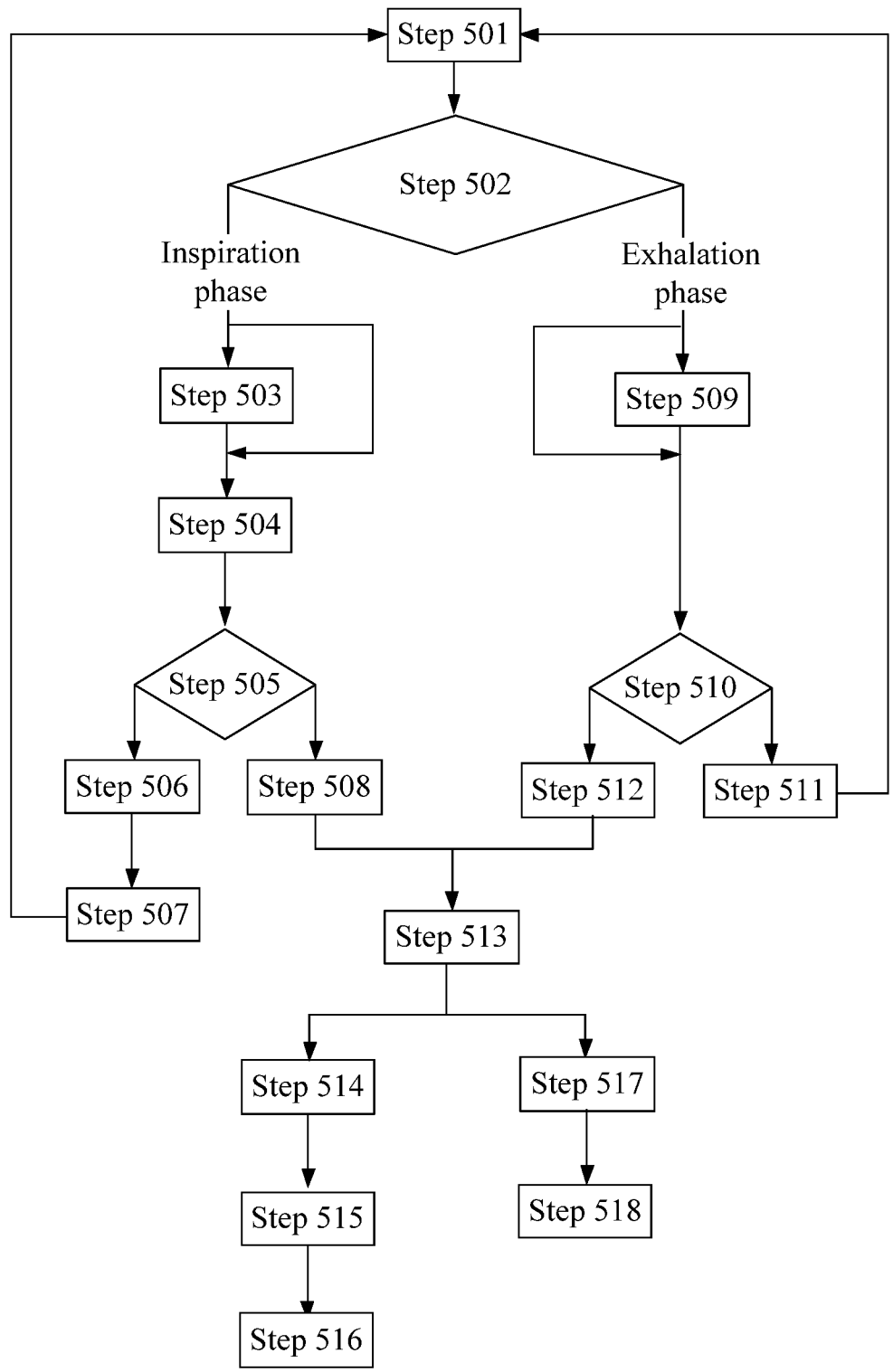
FIG. 5 is a schematic flowchart of a method for controlling an oxygen provider according to an embodiment of the present disclosure.

FIG. 5 is a schematic flowchart of a method for controlling an oxygen provider according to an embodiment of the present disclosure.

In the embodiment, a breathing in and out process is divided into two phases, which will be referred to as exhalation and inspiration, or an exhalation phase and an inspiration phase.

In an inspiration phase, the blended gas demand volume and the inspiration time are determined based on at least one of the flow measurement data or the pressure measurement data. In an exhalation phase, an exhalation time is determined based upon at least one of the flow measurement data or the pressure measurement data. Accordingly, a breathing period is a sum of the inspiration time and the exhalation time.

The method includes the steps as described in the following. Some of the steps which have already been explained in the embodiment corresponding to FIG. 2 will not be elaborated again for conciseness. The method may be applied in the oxygen delivering system shown in FIG. 1.

Step 501, a controller device acquires measurement data at a patient side.

The measurement data may include various physiology parameters of the patient. In a possible implementation, the measurement data includes flow measurement data and pressure measurement data. The measurement data may be acquired from a flow sensor and a pressure sensor attached in airway between the blower device and the patient.

Step 502, the controller device determines whether a current phase is exhalation or inspiration.

In the embodiment, a breathing in and out process is divided into two phases. In response to determining that the current phase is inspiration, execute step 503. In response to determining that the current phase is exhalation, execute step 509.

A current phase may change from inspiration to exhalation, or change from exhalation to inspiration. The process of a phase shift will be explained in the following steps.

An initial phase to begin with may be either exhalation or inspiration. For example, when the controller device is just powered up, it may be determined that a current phase is inspiration, and execute step 503. Or it may be determined that a current phase is exhalation, and execute step 509.

Step 503, the controller device triggers an inspiration timer.

The inspiration timer is triggered to count the duration of the inspiration phase.

Step 503 is executed when the inspiration timer is not triggered, and is skipped when the inspiration timer is already counting.

Step 504, the controller device calculates a patient flow based on the flow measurement data.

A portion of the blended gas flow output by the blower device is breathed in by the patient, this portion is referred to as a patient flow. Another portion of the blended gas flow is leaked out, this portion is referred to as a leak flow. The patient flow may be calculated according to equation 3.

$$F(\text{patient}) = F(\text{gas}) - F(\text{leakage}) \qquad \text{Equation 3}$$

Where F(patient) is the patient flow, F(gas) is the blended gas flow, and F(leakage) is the leak flow, which may be calculated according to Equation 4.

$$F(\text{leakage}) = \operatorname{sqrt}(Paw/c) \qquad \text{Equation 4}$$

Where Paw is a pressure in airway between the blower device and the patient (for example, the pressure at the patient interface), and c is a predetermined constant which may be contingent on a leaking property of the patient interface.

As the flow measurement data is dynamically updated (see step 507), the value of patient flow is dynamically updated accordingly.

Step 505, the controller device determines whether a first condition is satisfied.

A first condition is used as a trigger condition for a phase shift from inspiration to exhalation.

Since a transition from an inspiration to an exhalation causes the patient flow to drop, a drop of patient flow may be used as a trigger condition for a phase shift from an inspiration phase to an exhalation phase.

In a possible implementation, the first condition is that the patient flow is below a flow threshold, where the flow threshold may be determined based on a maximum patient flow which is a maximum value selected from the patient flow values recorded in the current inspiration phase.

For example, the flow threshold is 20% of the maximum patient flow or any other predefined values, when the patient flow is below the flow threshold, the controller device determines that the first condition is satisfied.

Alternatively, since a transition from an inspiration to an exhalation causes the pressure at the patient interface to rise, a rise of pressure may be used as a trigger condition for a phase shift from an inspiration phase to an exhalation phase.

In a possible implementation, the first condition is that P(rise) which is an increase of a current pressure, is above a pressure rise threshold, where the pressure rise threshold may be a predetermined value or a value input by a caregiver, and P(rise) is calculated according to Equation 5.

$$P(rise) = P(current) - P(baseline) \qquad \text{Equation 5}$$

Where P(current) is the current pressure, P(baseline) may be an average pressure value of the pressure values recorded in the current inspiration phase. When P(rise) is above the pressure rise threshold, the controller device determines that the first condition is satisfied.

When the first condition is not satisfied, execute step 506. When the first condition is satisfied, execute step 508.

Step 506, the controller device accumulates the patient flow as the blended gas demand volume.

In the current inspiration phase, the patient flow is dynamically updated (see step 507). If a phase shift is not triggered in step 505 (the current phase is still inspiration), the values of the patient flow recorded in the current inspiration phase are accumulated, to generate an integral value as the blended gas consumption volume in the current inspiration phase in totality. In the embodiment, the integral value is determined as the blended gas demand volume for a following breathing period.

Step 507, the controller device updates the flow measurement data and/or the flow measurement data.

In the embodiment, measurement data is dynamically updated. For example, step 501 is triggered every 10 milliseconds, or any other value that is selected or input by a caregiver.

In a possible implementation, when step 501 is executed, either or both of the flow measurement data and the pressure measurement data are dynamically updated, accordingly, parameters which are calculated based on the flow measurement data or the pressure measurement data, such as the patient flow, the maximum patient flow, the current pressure or the baseline pressure, are also updated.

Step 508, the controller device takes a value of the inspiration timer as the inspiration time and resetting the inspiration timer, and changes the current phase into exhalation.

When the first condition is satisfied, the current value of the inspiration timer is determined as the inspiration time, the current phase is changed from the inspiration phase into exhalation phase, and execute step 502.

Step 509, the controller device triggers an exhalation timer.

The exhalation timer is triggered to count the duration of the exhalation phase.

Step 509 is executed when the exhalation timer is not triggered, and is skipped when the exhalation timer is already counting.

Step 510, the controller device determines whether a second condition is satisfied.

A second condition is used as a trigger condition for a phase shift from exhalation to inspiration.

Since a transition from an exhalation to an inspiration causes the pressure at the patient interface to drop, a drop of pressure may be used as a trigger condition for a phase shift from an exhalation phase to an inspiration phase.

In a possible implementation, the second condition is that the pressure change is above a pressure drop threshold, where the pressure drop threshold may be a predetermined value or a value input by a caregiver, and the pressure change is calculated according to Equation 6.

$$P(change) = P(baseline) - P(current) \qquad \text{Equation 6}$$

Where P(change) is the pressure change which is a reduction from P(baseline) to P(current). When P(change) is above the pressure drop threshold, the controller device determines that the second condition is satisfied.

Alternatively, since a transition from an exhalation to an inspiration causes the patient flow to rise, a rise of the patient flow may be used as a trigger condition for a phase shift from an exhalation phase to an inspiration phase.

In a possible implementation, the second condition is that a rise of the patient flow is above a flow rise threshold, where the flow rise threshold may be a predetermined value or a value input by a caregiver, and the rise of the patient flow may be calculated according to Equation 7.

$$F(rise) = F(patient\_a) - F(patient\_b) \qquad \text{Equation 7}$$

Where F(rise) is the increase of the patient flow, F(patient_a) is a current value of the patient flow, and F(patient_b) is a recorded value in current exhalation phase. When F(rise) is above the flow rise threshold, the controller device determines that the second condition is satisfied.

When the second condition is not satisfied, execute step 511. When the second condition is satisfied, execute step 512.

It is noted that, the trigger condition for a phase shift explained in the above embodiment (the first condition as explained in step 505, or the second condition as explained in step 510) is just exemplary. The trigger condition may be contingent on various parameters, a person skilled in the art may obtain other trigger conditions based on the present disclosure.

Step 511, the controller device updates the pressure measurement data and/or the flow measurement data.

In the embodiment, measurement data is dynamically updated. In a possible implementation, step 501 is triggered every 10 milliseconds.

In a possible implementation, when step 501 is executed, either or both of the flow measurement data and the pressure measurement data are dynamically updated, accordingly, parameters which are calculated based on the flow measurement data or the pressure measurement data, such as the patient flow, the maximum patient flow, the current pressure or the baseline pressure, are also updated.

Step 512, the controller device takes a value of the exhalation timer as the exhalation time and resetting the exhalation timer, and changes the current phase into inspiration.

When the second condition is satisfied, the current value of the exhalation timer is determined as the exhalation time, the current phase is changed from the exhalation phase into inspiration phase, and execute step 502.

Step 513, the controller device determines the breathing period based on the inspiration time and the exhalation time.

In a possible implementation, the breathing period is a sum of the inspiration time and the exhalation time, where the inspiration time is determined in step 508, and the exhalation time is determined in step 512.

The process for the controller device to control the oxygen source is explained in the following steps 514 to 516, and the process for the controller device to control the blower device is explained in the following steps 517 to 518.

Step 514, the controller device determines the oxygen demand volume based on the blended gas demand volume and the desired oxygen fraction ratio.

In a possible implementation, the oxygen demand volume is calculated according to equation 1.

Step 515, the controller device determines a duty cycle of a controlling signal of an oxygen source.

In the embodiment, the controller device controls the output of the oxygen source with a pulse width modulation (PWM) controlling signal.

In a possible implementation, the initial duty cycle of the controlling signal is a predetermined value, and the duty cycle is dynamically adjusted.

For example, an oxygen concentration sensor is configured to detect the oxygen concentration of the blended gas in the airway between the blower device and the patient. In a situation where the oxygen source is switched on when the controlling signal level is of a relatively high amplitude, and the oxygen source is switched off when the controlling signal level is of a relatively low amplitude, when the oxygen concentration feedback by the oxygen concentration sensor is lower than a first concentration threshold (which may be an empirical value or a value input by a caregiver, for example, $FiO_2*95\%$), the controller device increases the duty cycle of the controlling signal by a predetermined scale; when the oxygen concentration feedback by the oxygen concentration sensor is higher than a second concentration threshold (which may be an empirical value or a value input by a caregiver, for example, $FiO_2*105\%$), the controller device decreases the duty cycle of the controlling signal by the predetermined scale.

In another possible implementation, the duty cycle of the PWM controlling signal is determined based on the oxygen demand volume and the inspiration time.

For example, the duty cycle during the inspiration time is calculated according to Equation 8.

$$D(inspiration) = F(\text{oxygen\_ins}) * \frac{T(pulse)}{V(pulse)} \qquad \text{Equation 8}$$

Where D(inspiration) is the duty cycle during the inspiration time Ti, T(pulse) is a duration for a PWM pulse, V(pulse) is an oxygen volume output by the oxygen source per PWM pulse, and F(oxygen_ins) is the oxygen flow output by the oxygen source during the inspiration time Ti. F(oxygen_ins) may be a ratio between the oxygen demand volume and the inspiration time. Or, considering that a portion of oxygen output by the oxygen source is leaked, F(oxygen_ins) may be a sum of the ratio and a bias oxygen flow which is a predetermined value or a value input by a caregiver.

During the exhalation time Tr, the oxygen source may be switched off, that is, the duty cycle during the exhalation time Tr is 0 (as shown in FIG. 4). Or, the duty cycle during the exhalation time Tr may be a minimum duty cycle to maintain a wash out gas flow in a breathing tube during the exhalation time Tr, where the minimum duty cycle may be a predetermined value or a value input by a caregiver.

Step 516, the controller device controls the oxygen source to operate according to the duty cycle.

In a possible implementation, the controller device includes an on-off solenoid to generate the PWM controlling signal of the duty cycle, so as to control the oxygen source to provide oxygen whose amount is defined by the oxygen demand volume. At the oxygen source side, upon receiving the PWM controlling signal, the oxygen source may work accordingly under the control of the PWM controlling signal.

Step 517, the controller device determines the output pattern based on the blended gas demand volume and the inspiration time.

In a possible implementation, the oxygen provider includes a blower device, and the output pattern includes a blower flow and a blowing period of the blower device.

The blower flow during the inspiration time Ti may be calculated according to Equation 2.

With reference to FIG. 4, the blowing period consists of a first time span Tb and a second time span Tn. The blowing period may be equal to the breathing period Ts, and the first time span may be equal to the inspiration time Ti. Accordingly, the second span Tn is equal to the exhalation time Tr.

It is noted that step 517 and step 514 are both triggered after step 513, and they may be triggered simultaneously.

Step 518, the controller device controls the blower device to operate according to the blower flow and the blowing period.

In a possible implementation, with reference to FIG. 4, the controller device controls the blower device to deliver the blended gas to a patient in each inspiration phase. At the blower device side, upon receiving ambient air by virtue of the accumulator, the blower device may work according to the determined blower flow and blowing period.

For example, during the first time span Tb, the controller device controls the blower device to blow blended gas to the patient according to the blower flow.

During the second time span Tn, the controller device controls the blower device to stop blowing, or to blow a wash out gas flow in a breathing tube during the second time span Tn, where the wash out gas flow may be a predetermined value or a value input by a caregiver, the operating speed of the blower device is as illustrated in FIG. 4 for an example.

The controller device may be communicatively connected to the blower device directly or indirectly. For example, the controller device may control the blower device via a direct communication connection which may be a wired connection or a wireless connection like Bluetooth connection. Or the controller device may send controlling parameters (for example, the blower flow and the blowing period) to the oxygen source, and the oxygen source controls the blower device according to the controlling parameters. The implementation of the communication connection between the controlling device and the blower device is not specifically limited, as long as the blower device is controlled by the controlling device according to the blower flow and the blowing period.

The blower flow may be dynamically adjusted. For example, a flow sensor may be attached at an output of the blower device to detect the blended gas flow. When the blended gas flow feedback by the flow sensor is lower than a first delivery threshold (which may be an empirical value or a value input by a caregiver, for example, F(gas)*95%), the controller device controls the blower device to increase the blended gas flow at the output of the blower device. When the oxygen concentration is higher than a second delivery threshold (which may be an empirical value or a value input by a caregiver, for example, F(gas)*105%), the controller device controls the blower device to decrease the blended gas flow at the output of the blower device.

According to the method for controlling an oxygen provider explained in the embodiments of the present disclosure, an oxygen demand volume as needed by a patient and an output pattern of an oxygen provider are determined, and the oxygen provider is controlled with the oxygen demand volume and the output pattern.

In one breathing period, oxygen with an amount that actually needed by the patient is provided to produce the blended gas to be delivered to the patient, and the blended gas delivered to the patient are regulated according to the output pattern to guarantee the blended gas is delivered to the patient during the inspiration time span.

In one breathing period, the amount of oxygen provided to the patient, and the output pattern of the oxygen provider may be different from that of a previous breathing period based on variation of the measurement data acquired at the patient side, therefore, the amount of oxygen provided to the patient, the blended gas delivered to the patient, and the output pattern of the oxygen provider may be dynamically adjusted.

In summary, the amount of oxygen and the blended gas actually needed by the patient is delivered and dynamically adjusted in synchronization with the inspiration of the patient, so that a therapeutic effect is achieved with a lower oxygen consumption amount.

Figure 6:
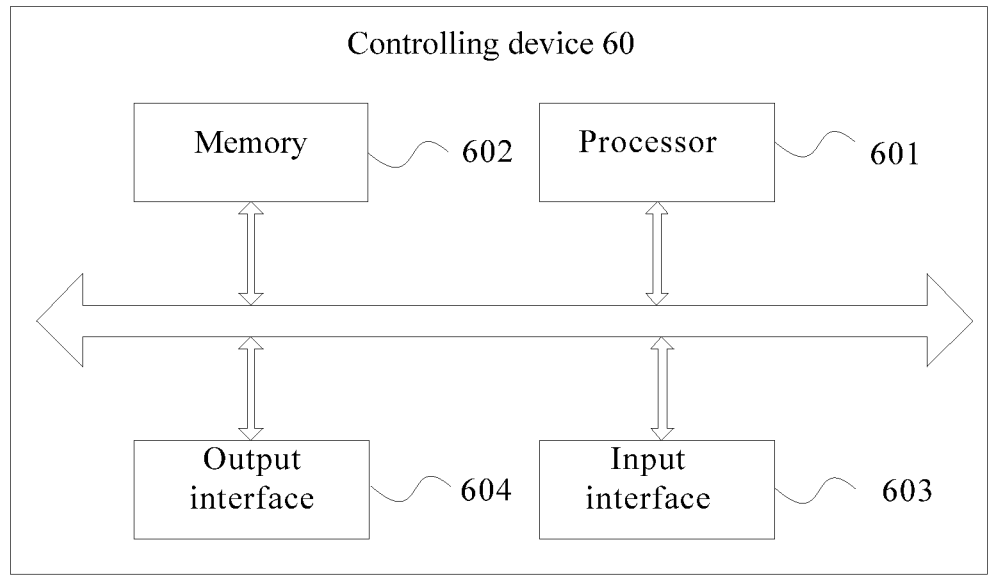
FIG. 6 is a schematic structural diagram of a controlling device according to an embodiment of the present disclosure.

FIG. 6 is a structural diagram of a controlling device 60 according to an embodiment of the present disclosure. the controlling device 60 is communicatively connected to an oxygen provider, and the controlling device 60 includes: at least one processor 601, and a memory 602 communicatively connected with the at least one processor 601; where the memory 602 stores instructions executable by the at least one processor 601, and the instructions, when executed by the at least one processor 601, cause the at least one processor 601 to:

acquire measurement data at a patient side;

determine an oxygen demand volume and an output pattern of an oxygen provider based on the acquired measurement data and a desired oxygen fraction ratio; and control the oxygen provider with the oxygen demand volume and the output pattern.

In a possible implementation, the controlling device 60 further includes an input interface 603 and an output interface 604.

The input interface 603 is configured to receive input signals of the controlling device 60, which includes but not limited to signals generated from the patient such as signals indicating various physiology parameters of the patient.

The output interface 604 is configured to output signals of the controlling device 60, which includes the controlling signal to the oxygen provider as explained in the embodiment of the controlling method.

In a possible implementation, the at least one processor 601 is caused to:

determine a blended gas demand volume, an inspiration time and a breathing period based on the measurement data of the patient;

determine the oxygen demand volume based on the blended gas demand volume and the desired oxygen fraction ratio; and determine the output pattern based on the blended gas demand volume, the inspiration time and the breathing period.

In a possible implementation, the oxygen provider includes an oxygen source and a blower device, the oxygen source is communicatively connected to the controlling device and the blower device is connected to the oxygen source;

the output pattern includes a blower flow and a blowing period of the blower device;

the at least one processor 601 is caused to determine the blower flow based on the blended gas demand volume and the inspiration time, and determine the blowing period based on the inspiration time and the breathing period;

the at least one processor 601 is caused to:

determine a duty cycle of the oxygen source based on the oxygen demand volume and the inspiration time;

control the oxygen source to operate according to the duty cycle; and control the blower device to operate according to the blower flow and the blowing period.

In a possible implementation, the at least one processor 601 is caused to:

obtain oxygen concentration measurement data at an output of the blower device; and determine the oxygen demand volume based on the blended gas demand volume, the desired oxygen fraction ratio and the obtained oxygen measurement data.

In a possible implementation, the at least one processor 601 is caused to:

obtain flow measurement data at an output of the blower device; and determine the blower flow based on the blended gas demand volume, the inspiration time and the obtained flow measurement data.

In a possible implementation, the measurement data includes flow measurement data and pressure measurement data;

where the at least one processor 601 is caused to:

determine whether a current phase is exhalation or inspiration;

in response to determining that the current phase is inspiration, determine the blended gas demand volume and the inspiration time based on at least one of the flow measurement data or the pressure measurement data;

in response to determining that the current phase is exhalation, determine an exhalation time based on the pressure measurement data; and determine the breathing period based on the inspiration time and the exhalation time.

In a possible implementation, the at least one processor 601 is caused to:

in response to determining that the current phase is inspiration, trigger an inspiration timer and execute following steps until a first condition is satisfied:

calculate a patient flow and a maximum patient flow based on the flow measurement data; determine whether the patient flow is below a flow threshold, the flow threshold being determined based on the maximum patient flow; and in response to determining that the patient flow is blew the flow threshold, determine that the first condition is satisfied; otherwise, the at least one processor 601 is caused to:

accumulate the patient flow as the blended gas demand volume and update the flow measurement data;

when the first condition is satisfied, take a value of the inspiration timer as the inspiration time and reset the inspiration timer; and change the current phase into exhalation.

In a possible implementation, the at least one processor 601 is caused to:

in response to determining that the current phase is inspiration, trigger an inspiration timer and execute following steps until a first condition is satisfied:

calculate a patient flow based on the flow measurement data;

calculate a current pressure and a baseline pressure based on the pressure measurement data; determine whether an increase of the current pressure from the baseline pressure is above a pressure rise threshold; and in response to determining that the increase of the current pressure is above the pressure rise threshold, determine that the first condition is satisfied; otherwise, the at least one processor 601 is caused to:

accumulate the patient flow as the blended gas demand volume and update the flow measurement data and the pressure measurement data;

when the first condition is satisfied, take a value of the inspiration timer as the inspiration time and reset the inspiration timer; and change the current phase into exhalation.

In a possible implementation, the at least one processor 601 is caused to:

in response to determining that the current phase is exhalation, trigger an exhalation timer and execute following steps until a second condition is satisfied:

calculate a pressure change based on the pressure measurement data; determine whether the pressure change is above a pressure drop threshold; and in response to determining that the pressure change is above the pressure drop threshold, determine that the second condition is satisfied; otherwise, the at least one processor 601 is caused to:

update the pressure measurement data;

when the second condition is satisfied, take a value of the exhalation timer as the exhalation time and reset the exhalation timer; and change the current phase into inspiration.

In a possible implementation, the at least one processor 601 is caused to:

in response to determining that the current phase is exhalation, trigger an exhalation timer and execute following steps until a second condition is satisfied:

calculate a patient flow increase based on the flow measurement data; determine whether the patient flow increase is above a flow rise threshold; and in response to determining that the patient flow increase is above the flow rise threshold, determine that the second condition is satisfied; otherwise, the at least one processor 601 is caused to:

update the flow measurement data;

when the second condition is satisfied, take a value of the exhalation timer as the exhalation time and reset the exhalation timer; and change the current phase into inspiration.

Figure 7:
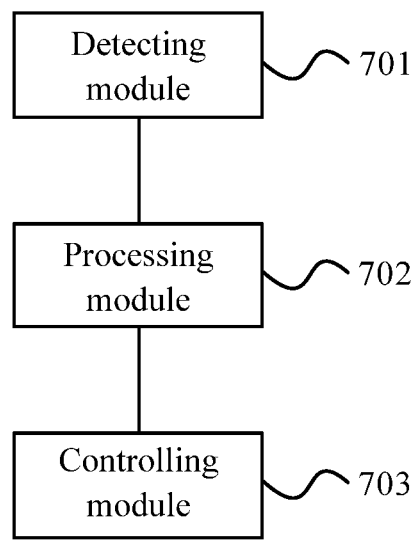
FIG. 7 is a schematic diagram of a controlling device according to an embodiment of the present disclosure.

FIG. 7 is a schematic diagram of a controlling device 70 according to an embodiment of the present disclosure. The controlling device 70 is communicatively connected to an oxygen provider, and the controlling device 70 includes: a detecting module 701, a processing module 702 and a controlling module 703.

The detecting module 701 is configured to acquire measurement data at a patient side;

The processing module 702 is configured to determine an oxygen demand volume and an output pattern of an oxygen provider based on the acquired measurement data and a desired oxygen fraction ratio; and The controlling module 703 is configured to control the oxygen provider with the oxygen demand volume and the output pattern.

In a possible implementation, the processing module 702 is specifically configured to: determine a blended gas demand volume, an inspiration time and a breathing period based on the measurement data of the patient; determine the oxygen demand volume based on the blended gas demand volume and the desired oxygen fraction ratio; and determine the output pattern based on the blended gas demand volume, the inspiration time and the breathing period.

In a possible implementation, the oxygen provider includes an oxygen source and a blower device, the oxygen source is communicatively connected to the controlling device 70 and the blower device is connected to the oxygen source; the output pattern includes a blower flow and a blowing period of the blower device.

The processing module 702 is specifically configured to determine the blower flow based on the blended gas demand volume and the inspiration time, and determine the blowing period based on the inspiration time and the breathing period.

The controlling module 703 is specifically configured to determine a duty cycle of the oxygen source based on the oxygen demand volume and the inspiration time; control the oxygen source to operate according to the duty cycle; and control the blower device to operate according to the blower flow and the blowing period.

In a possible implementation, the processing module 702 is specifically configured to obtain oxygen concentration measurement data at an output of the blower device; and determine the oxygen demand volume based on the blended gas demand volume, the desired oxygen fraction ratio and the obtained oxygen measurement data.

In a possible implementation, the controlling module 703 is specifically configured to obtain flow measurement data at an output of the blower device; and determine the blower flow based on the blended gas demand volume, the inspiration time and the obtained flow measurement data.

In a possible implementation, the measurement data includes flow measurement data and pressure measurement data; the processing module 702 is specifically configured to determine whether a current phase is exhalation or inspiration; in response to determining that the current phase is inspiration, determine the blended gas demand volume and the inspiration time based on at least one of the flow measurement data or the pressure measurement data; in response to determining that the current phase is exhalation, determine an exhalation time based on the pressure measurement data; and determine the breathing period based on the inspiration time and the exhalation time.

In a possible implementation, the processing module 702 is specifically configured to: in response to determining that the current phase is inspiration, trigger an inspiration timer and execute following steps until a first condition is satisfied:

calculate a patient flow and a maximum patient flow based on the flow measurement data; determine whether the patient flow is below a flow threshold, the flow threshold being determined based on the maximum patient flow; and in response to determining that the patient flow is blew the flow threshold, determine that the first condition is satisfied; otherwise, the processing module 702 is further configured to:

accumulate the patient flow as the blended gas demand volume and update the flow measurement data; take a value of the inspiration timer as the inspiration time and reset the inspiration timer when the first condition is satisfied; and change the current phase into exhalation.

In a possible implementation, the processing module 702 is specifically configured to: in response to determining that the current phase is inspiration, trigger an inspiration timer and execute following steps until a first condition is satisfied:

in response to determining that the current phase is inspiration, trigger an inspiration timer and execute following steps until a first condition is satisfied:

calculate a patient flow and a maximum patient flow based on the flow measurement data; determine whether the patient flow is below a flow threshold, the flow threshold being determined based on the maximum patient flow; and in response to determining that the patient flow is blew the flow threshold, determine that the first condition is satisfied; otherwise, the processing module 702 is further configured to:

accumulate the patient flow as the blended gas demand volume and update the flow measurement data;

when the first condition is satisfied, take a value of the inspiration timer as the inspiration time and reset the inspiration timer; and change the current phase into exhalation.

In a possible implementation, the processing module 702 is specifically configured to, in response to determining that the current phase is exhalation, trigger an exhalation timer and execute following steps until a second condition is satisfied:

calculate a pressure change based on the pressure measurement data; determine whether the pressure change is above a pressure drop threshold; and in response to determining that the pressure change is above the pressure drop threshold, determine that the second condition is satisfied; otherwise, the processing module 702 is further configured to:

update the pressure measurement data; take a value of the exhalation timer as the exhalation time and reset the exhalation timer when the second condition is satisfied; and change the current phase into inspiration.

In a possible implementation, the processing module 702 is specifically configured to, in response to determining that the current phase is exhalation, trigger an exhalation timer and execute following steps until a second condition is satisfied:

in response to determining that the current phase is exhalation, trigger an exhalation timer and execute following steps until a second condition is satisfied:

calculate a patient flow increase based on the flow measurement data; determine whether the patient flow increase is above a flow rise threshold; and in response to determining that the patient flow increase is above the flow rise threshold, determine that the second condition is satisfied; otherwise, the processing module 702 is further configured to:

update the flow measurement data;

when the second condition is satisfied, take a value of the exhalation timer as the exhalation time and reset the exhalation timer; and change the current phase into inspiration.

Figure 8:
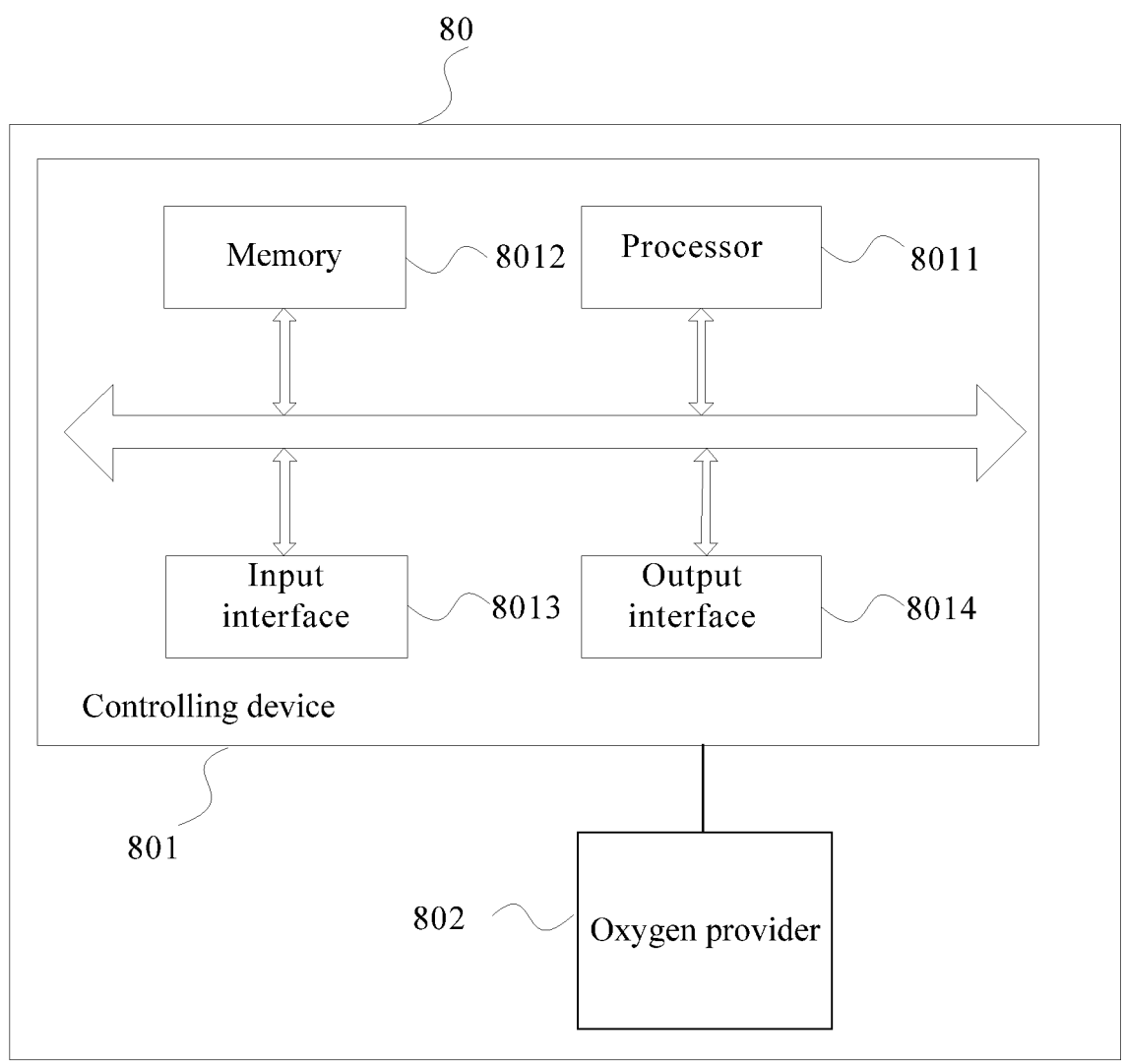
FIG. 8 is a schematic diagram of a portable device according to an embodiment of the present disclosure.

FIG. 8 is a schematic diagram of a portable device 80 according to an embodiment of the present disclosure. The portable device 80 includes a controlling device 801 and an oxygen provider 802 being communicatively connected to each other.

the controlling device 801 includes at least one processor 8011, and a memory 8012 communicatively connected with the at least one processor 8011, where the memory 8012 stores instructions executable by the at least one processor 8011, and the instructions, when executed by the at least one processor 8011, cause the at least one processor 8011 to:

acquire measurement data at a patient side;

determine an oxygen demand volume and an output pattern of an oxygen provider based on the acquired measurement data and a desired oxygen fraction ratio; and control the oxygen provider with the oxygen demand volume and the output pattern.

In a possible implementation, the controlling device 801 further includes an input interface 8013 and an output interface 8014.

The input interface 8013 is configured to receive input signals of the controlling device 801, which includes but not limited to signals generated from the patient such as signals indicating various physiology parameters of the patient.

The output interface 8013 is configured to output signals of the controlling device 801, which includes the controlling signal to the oxygen provider as explained in the embodiment of the controlling method.

In a possible implementation, the at least one processor 8011 is caused to:

determine a blended gas demand volume, an inspiration time and a breathing period based on the measurement data of the patient;

determine the oxygen demand volume based on the blended gas demand volume and the desired oxygen fraction ratio; and determine the output pattern based on the blended gas demand volume and the inspiration time.

In a possible implementation form of the portable device according to the fourth aspect as such, where the oxygen provider includes an oxygen source and a blower device, the oxygen source is communicatively connected to the controlling device 801 and the blower device is connected to the oxygen source;

the output pattern includes a blower flow and a blowing period of the blower device;

the at least one processor 8011 is caused to determine the blower flow based on the blended gas demand volume and the inspiration time, and determine the blowing period based on the inspiration time and the breathing period;

the at least one processor 8011 is caused to:

determine a duty cycle of the oxygen source based on the oxygen demand volume and the inspiration time;

control the oxygen source to operate according to the duty cycle; and control the blower device to operate according to the blower flow and the blowing period.

In a possible implementation, the at least one processor 8011 is caused to:

obtain oxygen concentration measurement data at an output of the blower device;

and determine the oxygen demand volume based on the blended gas demand volume, the desired oxygen fraction ratio and the obtained oxygen measurement data.

In a possible implementation, the at least one processor 8011 is caused to:

obtain flow measurement data at an output of the blower device; and determine the blower flow based on the blended gas demand volume, the inspiration time and the obtained flow measurement data.

In a possible implementation form of the portable device according to the fourth aspect as such, where the measurement data includes flow measurement data and pressure measurement data;

where the at least one processor 8011 is caused to:

determine whether a current phase is exhalation or inspiration;

in response to determining that the current phase is inspiration, determine the blended gas demand volume and the inspiration time based on at least one of the flow measurement data or the pressure measurement data;

in response to determining that the current phase is exhalation, determine an exhalation time based on the pressure measurement data; and determine the breathing period based on the inspiration time and the exhalation time.

In a possible implementation, the at least one processor 8011 is caused to:

in response to determining that the current phase is inspiration, trigger an inspiration timer and execute following steps until a first condition is satisfied:

calculate a patient flow and a maximum patient flow based on the flow measurement data; determine whether the patient flow is below a flow threshold, the flow threshold being determined based on the maximum patient flow; and in response to determining that the patient flow is blew the flow threshold, determine that the first condition is satisfied; otherwise, the at least one processor 8011 is caused to:

accumulate the patient flow as the blended gas demand volume and update the flow measurement data;

when the first condition is satisfied, take a value of the inspiration timer as the inspiration time and reset the inspiration timer; and change the current phase into exhalation.

In a possible implementation, the at least one processor 8011 is caused to:

in response to determining that the current phase is inspiration, trigger an inspiration timer and executing following steps until a first condition is satisfied:

calculate a patient flow based on the flow measurement data;

calculate a current pressure and a baseline pressure based on the pressure measurement data; determine whether an increase of the current pressure from the baseline pressure is above a pressure rise threshold; and in response to determining that the increase of the current pressure is above the pressure rise threshold, determine that the first condition is satisfied; otherwise, the at least one processor 8011 is caused to:

accumulate the patient flow as the blended gas demand volume and update the flow measurement data and the pressure measurement data;

when the first condition is satisfied, take a value of the inspiration timer as the inspiration time and reset the inspiration timer; and change the current phase into exhalation.

In a possible implementation, the at least one processor 8011 is caused to:

in response to determining that the current phase is exhalation, trigger an exhalation timer and execute following steps until a second condition is satisfied:

calculate a pressure change based on the pressure measurement data; determine whether the pressure change is above a pressure drop threshold; and in response to determining that the pressure change is above the pressure drop threshold, determining that the second condition is satisfied; otherwise, the at least one processor 8011 is caused to:

update the pressure measurement data;

when the second condition is satisfied, take a value of the exhalation timer as the exhalation time and reset the exhalation timer; and change the current phase into inspiration.

In a possible implementation, the at least one processor 8011 is caused to:

in response to determining that the current phase is exhalation, trigger an exhalation timer and execute following steps until a second condition is satisfied:

calculate a patient flow increase based on the flow measurement data; determine whether the patient flow increase is above a flow rise threshold; and in response to determining that the patient flow increase is above the flow rise threshold, determine that the second condition is satisfied; otherwise, the at least one processor 8011 is caused to:

update the flow measurement data;

when the second condition is satisfied, take a value of the exhalation timer as the exhalation time and reset the exhalation timer; and change the current phase into inspiration.

The present disclosure also provides a computer readable storage medium, storing thereon computer executable instructions which, when being executed by a processor, implement the method for controlling an oxygen provider described above.

Terms such as "first", "second" and the like in the specification and claims of the present disclosure as well as in the above drawings are intended to distinguish different objects, but not intended to define a particular order.

The term "a" or "an" is not intended to specify one or a single element, instead, it may be used to represent a plurality of elements where appropriate.

In one or more examples, the functions described may be implemented in hardware, software, firmware, or any combination thereof. For example, the functions may be implemented by one or more processors, such as one or more application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, the techniques could be fully implemented in one or more circuits or logic elements.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate, preclude or suggest that a combination of these measures cannot be used to advantage.

The foregoing detailed description has been presented for purposes of illustration and description. It is not intended to be exhaustive or to limit the subject matter claimed herein to the precise form(s) disclosed. Many modifications and variations are possible in light of the above teachings. The described embodiments were chosen in order to best explain the principles of the disclosed technology and its practical application to thereby enable others skilled in the art to best utilize the technology in various embodiments and with various modifications as are suited to the particular use contemplated. Those embodiments with various modifications are within the range and scope of the following claims.

What is claimed is:

1. A method for controlling an oxygen provider, comprising:
acquiring measurement data at a patient side of the oxygen provider, wherein the oxygen provider comprises an oxygen source and a blower device;
determining an oxygen demand volume and an output pattern of the blower device based on the acquired measurement data and a desired oxygen fraction ratio, wherein the output pattern comprises a blowing period, a blower flow and a wash out flow of the blower device, and the blowing period comprises a first time span and a second time span;
controlling the oxygen source with the oxygen demand volume;
controlling the blower device with the blower flow to output blended gas in the first time span, wherein the blended gas is a mixture of oxygen and air; and
controlling the blower device with the wash out flow in the second time span;
wherein determining the oxygen demand volume and the output pattern of the blower device based on the acquired measurement data and the desired oxygen fraction ratio comprises:
determining a blended gas demand volume, an inspiration time and a breathing period based on the measurement data;
determining the oxygen demand volume based on the blended gas demand volume and the desired oxygen fraction ratio; and
determining the output pattern of the blower device based on the blended gas demand volume, the inspiration time and the breathing period;
wherein determining the output pattern of the blower device based on the blended gas demand volume, the inspiration time and the breathing period comprises:
determining the blower flow based on the blended gas demand volume and the inspiration time, and determining the blowing period based on the inspiration time and the breathing period;
wherein controlling the oxygen source with the oxygen demand volume comprises:
determining a duty cycle of the oxygen source based on the oxygen demand volume and the inspiration time; and
controlling the oxygen source to operate according to the duty cycle in the inspiration time.

2. The method according to claim 1, wherein determining the oxygen demand volume based on the blended gas demand volume and the desired oxygen fraction ratio comprises:
obtaining oxygen concentration measurement data at an output of the blower device; and
determining the oxygen demand volume based on the blended gas demand volume, the desired oxygen fraction ratio and the obtained oxygen concentration measurement data.

3. The method according to claim 1, wherein determining the blower flow based on the blended gas demand volume and the inspiration time comprises:
obtaining flow measurement data at an output of the blower device; and
determining the blower flow based on the blended gas demand volume, the inspiration time and the obtained flow measurement data.

4. The method according to claim 1, wherein the measurement data comprises flow measurement data and pressure measurement data;
determining the blended gas demand volume, the inspiration time and the breathing period based on the measurement data comprises:
determining whether a current phase is exhalation or inspiration;
in response to determining that the current phase is inspiration, determining the blended gas demand volume and the inspiration time based on at least one of the flow measurement data or the pressure measurement data;
in response to determining that the current phase is exhalation, determining an exhalation time based on at least one of the flow measurement data or the pressure measurement data; and
determining the breathing period based on the inspiration time and the exhalation time.

5. The method according to claim 4, wherein in response to determining that the current phase is inspiration, determining the blended gas demand volume and the inspiration time based on at least one of the flow measurement data or the pressure measurement data comprises:
in response to determining that the current phase is inspiration, triggering an inspiration timer and executing following steps until a first condition is satisfied:
calculating a patient flow and a maximum patient flow based on the flow measurement data; determining whether the patient flow is below a flow threshold, the flow threshold being determined based on the maximum patient flow; and
in response to determining that the patient flow is below the flow threshold, determining that the first condition is satisfied; otherwise,
accumulating the patient flow as the blended gas demand volume and updating the flow measurement data;
when the first condition is satisfied, taking a value of the inspiration timer as the inspiration time and resetting the inspiration timer; and changing the current phase into exhalation.

6. The method according to claim 4, wherein in response to determining that the current phase is inspiration, determining the blended gas demand volume and the inspiration time based on at least one of the flow measurement data or the pressure measurement data comprises:
in response to determining that the current phase is inspiration, triggering an inspiration timer and executing following steps until a first condition is satisfied:
calculating a patient flow based on the flow measurement data;
calculating a current pressure and a baseline pressure based on the pressure measurement data; determining whether an increase of the current pressure from the baseline pressure is above a pressure rise threshold, wherein the baseline pressure is an average pressure value of pressure values recorded in the current phase; and
in response to determining that the increase of the current pressure is above the pressure rise threshold, determining that the first condition is satisfied; otherwise,
accumulating the patient flow as the blended gas demand volume and updating the flow measurement data and the pressure measurement data;

when the first condition is satisfied, taking a value of the inspiration timer as the inspiration time and resetting the inspiration timer; and changing the current phase into exhalation.

7. The method according to claim 4, wherein in response to determining that the current phase is exhalation, determining the exhalation time based on at least one of the flow measurement data or the pressure measurement data comprises:
  in response to determining that the current phase is exhalation, triggering an exhalation timer and executing following steps until a second condition is satisfied:
    calculating a pressure change based on the pressure measurement data; determining whether the pressure change is above a pressure drop threshold, wherein the pressure change is a reduction of a current pressure from a baseline pressure, and the baseline pressure is an average pressure value of pressure values recorded in the current phase; and
    in response to determining that the pressure change is above the pressure drop threshold, determining that the second condition is satisfied; otherwise,
    updating the pressure measurement data;
  when the second condition is satisfied, taking a value of the exhalation timer as the exhalation time and resetting the exhalation timer; and changing the current phase into inspiration.

8. The method according to claim 4, wherein in response to determining that the current phase is exhalation, determining the exhalation time based on at least one of the flow measurement data or the pressure measurement data comprises:
  in response to determining that the current phase is exhalation, triggering an exhalation timer and executing following steps until a second condition is satisfied:
    calculating a patient flow increase based on the flow measurement data; determining whether the patient flow increase is above a flow rise threshold; and
    in response to determining that the patient flow increase is above the flow rise threshold, determining that the second condition is satisfied; otherwise,
    updating the flow measurement data;
  when the second condition is satisfied, taking a value of the exhalation timer as the exhalation time and resetting the exhalation timer; and changing the current phase into inspiration.

9. A computer readable storage medium, storing thereon computer executable instructions which, when being executed by a processor, implement the method for controlling an oxygen provider according to claim 1.

10. A controlling device, the controlling device is configured to communicatively connect to an oxygen provider, wherein the oxygen provider comprises an oxygen source and a blower device, and the controlling device comprises:
  at least one processor; and
  a memory communicatively connected with the at least one processor; wherein,
  the memory stores instructions executable by the at least one processor, and the instructions, when executed by the at least one processor, cause the at least one processor to:
  acquire measurement data at a patient side of the oxygen provider;
  determine an oxygen demand volume and an output pattern of the blower device based on the acquired measurement data and a desired oxygen fraction ratio, wherein the output pattern comprises a blowing period, a blower flow and a wash out flow of the blower device, and the blowing period comprises a first time span and a second time span;
  control the oxygen source with the oxygen demand volume;
  control the blower device with the blower flow to output blended gas in the first time span, wherein the blended gas is a mixture of oxygen and air; and
  control the blower device with the wash out flow in the second time span;
  wherein the at least one processor is caused to:
  determine a blended gas demand volume, an inspiration time and a breathing period based on the measurement data;
  determine the oxygen demand volume based on the blended gas demand volume and the desired oxygen fraction ratio; and
  determine the output pattern of the blower device based on the blended gas demand volume, the inspiration time and the breathing period;
  wherein the at least one processor is caused to:
  determine the blower flow based on the blended gas demand volume and the inspiration time, and determine the blowing period based on the inspiration time and the breathing period;
  determine a duty cycle of the oxygen source based on the oxygen demand volume and the inspiration time; and
  control the oxygen source to operate according to the duty cycle in the inspiration time.

11. The controlling device according to claim 10, wherein the at least one processor is caused to:
  obtain oxygen concentration measurement data at an output of the blower device; and
  determine the oxygen demand volume based on the blended gas demand volume, the desired oxygen fraction ratio and the obtained oxygen concentration measurement data.

12. The controlling device according to claim 10, wherein the measurement data comprises flow measurement data and pressure measurement data;
  wherein the at least one processor is caused to:
  determine whether a current phase is exhalation or inspiration;
  in response to determining that the current phase is inspiration, determine the blended gas demand volume and the inspiration time based on at least one of the flow measurement data or the pressure measurement data;
  in response to determining that the current phase is exhalation, determine an exhalation time based on the pressure measurement data; and
  determine the breathing period based on the inspiration time and the exhalation time.

13. A portable device, comprising a controlling device according to claim 10 and an oxygen provider being communicatively connected to each other.

14. A method for controlling an oxygen provider, comprising:
  acquiring measurement data at a patient side of the oxygen provider;
  determining an oxygen demand volume and an output pattern of the oxygen provider based on the acquired measurement data and a desired oxygen fraction ratio, wherein the output pattern comprises a blowing period, a blended gas flow and a wash out flow, and the blowing period comprises a first time span and a second time span;

controlling the oxygen provider with the oxygen demand volume to generate oxygen;
controlling the oxygen provider with the blended gas flow to output blended gas in the first time span, wherein the blended gas is a mixture of the generated oxygen and air; and
controlling the oxygen provider with the wash out flow in the second time span;
wherein determining the oxygen demand volume and the output pattern of the oxygen provider based on the acquired measurement data and the desired oxygen fraction ratio comprises:
  determining a blended gas demand volume, an inspiration time and a breathing period based on the measurement data;
  determining the oxygen demand volume based on the blended gas demand volume and the desired oxygen fraction ratio; and
  determining the output pattern of the oxygen provider based on the blended gas demand volume, the inspiration time and the breathing period;
wherein determining the output pattern of the oxygen provider based on the blended gas demand volume, the inspiration time and the breathing period comprises:
  determining the blended gas flow based on the blended gas demand volume and the inspiration time, and determining the blowing period based on the inspiration time and the breathing period;
wherein controlling the oxygen provider with the oxygen demand volume comprises:
  determining a duty cycle based on the oxygen demand volume and the inspiration time; and
controlling the oxygen provider to operate according to the duty cycle in the inspiration time.

* * * * *